United States Patent
Millar et al.

[11] Patent Number: 5,953,111
[45] Date of Patent: *Sep. 14, 1999

[54] CONTINUOUS IN-LINE KAPPA MEASUREMENT SYSTEM

[75] Inventors: Ord D. Millar, Pierrefonds, Canada; Richard J. Van Fleet, Cave Creek, Ariz.

[73] Assignee: Honeywell Inc., Minneapolis, Minn.

[*] Notice: This patent is subject to a terminal disclaimer.

[21] Appl. No.: 08/989,720

[22] Filed: Dec. 11, 1997

[51] Int. Cl.⁶ .................................................. G01N 21/64
[52] U.S. Cl. .............................................. 356/73; 356/425
[58] Field of Search ................................. 356/73, 42, 318

[56] References Cited

U.S. PATENT DOCUMENTS

| | | | |
|---|---|---|---|
| 3,994,602 | 11/1976 | Howarth | 356/435 |
| 4,222,064 | 9/1980 | Lodzinski | 356/73 |
| 5,220,172 | 6/1993 | Berthold et al. | 250/461.1 |
| 5,486,915 | 1/1996 | Jeffers et al. | 356/318 |

*Primary Examiner*—Robert H. Kim
*Assistant Examiner*—Zandra V. Smith
*Attorney, Agent, or Firm*—Anthony Miologos

[57] ABSTRACT

A system for the continual, real-time, in-situ generation of a Kappa number used by a process control system to control the delignification of papermaking pulps that includes injecting broad-spectrum light energy from a light energy source into the pulp and collecting the resultant reflected light energy from a near-and a far-light collector. The reflected light energy collected by the light collectors is analyzed by associated near- and far-light analyzers that generate analog output signals representing the intensity of selected wavelengths of light energy received by the light collectors. An included feedback arrangement conducts the light energy emitted by the light source to a location proximate the point of injection and then to an associated light analyzer that generates analog output signals representing the intensity of the light energy emitted by the light source in selected wavelengths. The output signals from the near-, far- and feedback-light analyzers are transmitted to a measurement processing system that converts the analog signals to digital signals and passes the signals to a measurement computer. The measurement computer, using preprogrammed algorithms, processes the received reflectance output signals along with previously-stored coefficient values that represent a model of the delignification or bleaching process, and along with configuration data, generates an output signal representing a Kappa number representation. The output signal from the measurement computer is converted by an input/output device into a signal form acceptable by the process control system, where it is used to control the delignification process in accordance to the Kappa number representation.

18 Claims, 4 Drawing Sheets

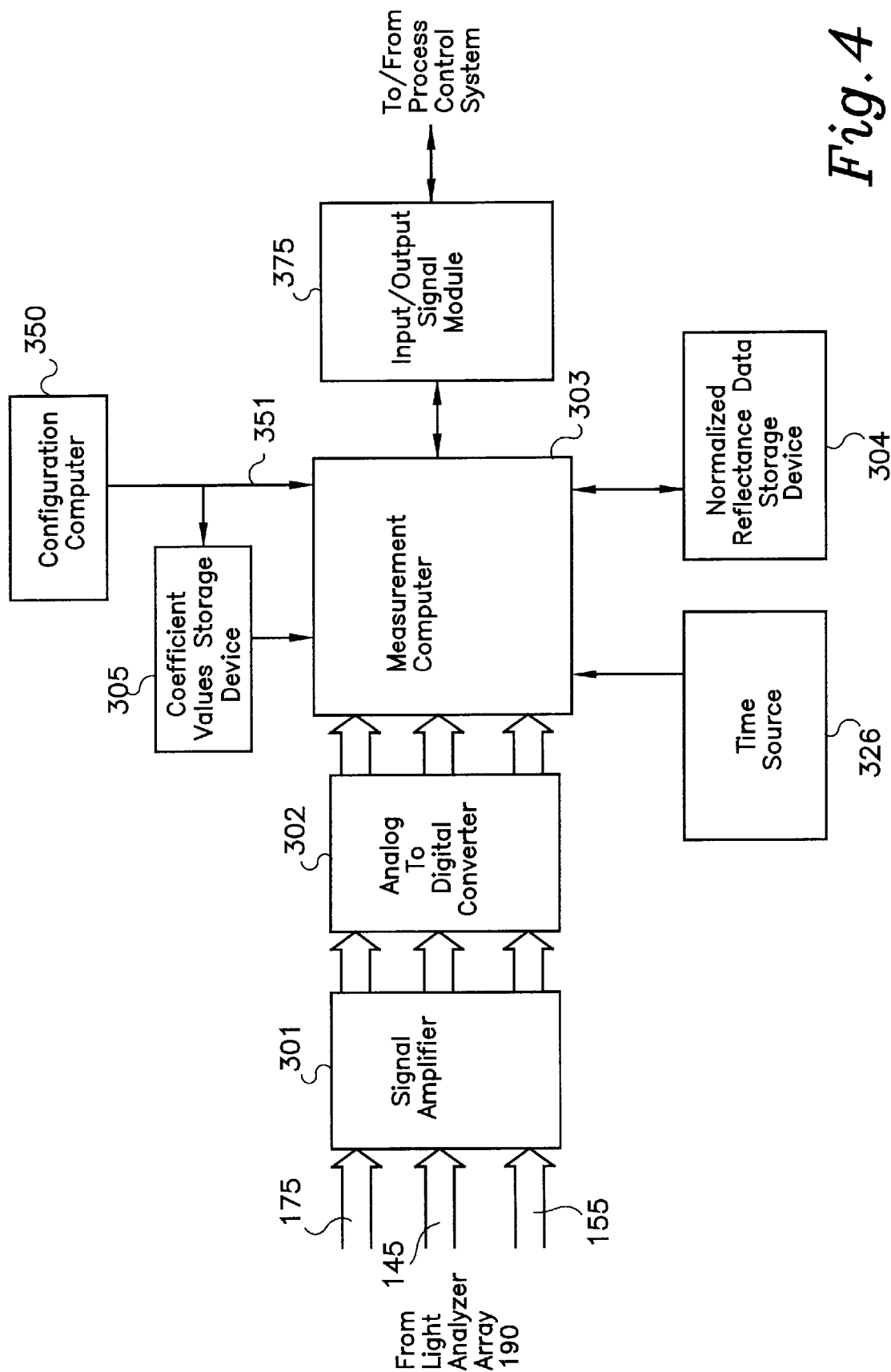

CONTINUOUS IN-LINE KAPPA MEASUREMENT SYSTEM

CROSS-REFERENCE TO RELATED APPLICATIONS

The present application is related to co-pending application, Ser. No. 08/988,972, titled "An Apparatus Used in Determining the Degree of Completion of a Processed Medium"; and co-pending application, Ser. No. 08/988,971, titled "A Method for Producing Continuous In-Line Kappa Measurements for Papermaking Pulps"; both applications filed on the same date herewith, and both applications having a common assignee as the present invention.

FIELD OF THE INVENTION

This invention relates in general to pulp and paper making and more particularly to a system for providing in-situ, and on a real-time basis, the Kappa number representation of the bleachability of papermaking pulps.

BACKGROUND OF THE INVENTION

In the pulp and paper industry, pulping refers to the process of converting wood chip feed stock into separate fibers by the chemical reaction between the lignin found in the wood chips and the active chemicals in a cooking liquor. This delignification process separates the wood cellulose fibers by breaking down the lignin. Lignin is a polymer of complex chemical structure which "cements" together the wood's cellulose fibers. The most prevalent method of delignification is by chemical means in which raw wood chips and chemicals are combined at a controlled pressure and temperature in a vessel known as a digester. While in the digester, the amount of lignin removed from the wood chips determines the product quality, the product yield, and the amount of energy consumed. Fluid drained from the digester during delignification contains lignin removed from the wood chips and is referred to in the industry as "black liquor". Black liquor is subsequently used to advantage during the pulping process as fuel in a boiler to produce process steam.

One common method of delignification presently used in pulp making is the kraft process. In this process, the wood chip feed stock is cooked with caustic soda and sodium sulfide, which removes most of the lignin without attacking the remaining cellulose fibers. When the remaining pulp of the kraft process is not passed through a bleaching process, it is used in cardboard or paper sack production. The dark color of this product is due to the remaining lignin in the fibers. However, if the final product of the process is to be a good-quality white paper, a bleaching step is introduced in the process, using chlorine, chlorine dioxide, oxygen, ozone, or hydrogen peroxide as the bleaching agent. The bleaching dissolves the remaining lignin and renders white the remaining cellulose fibers. The amount of whiteness and the term or amount of time that the final paper product remains white are dependent on the remaining residual lignin in the cellulose fibers. It is, therefore, customary to test the lignin content of the pulp fibers and use this determination as a measure of the effectiveness of the ongoing bleaching operation.

Predicting the bleachability of the pulp in the prior art has been by the use of one or more of the several available tests such as the Permanganate Number (TAPPI method T-214), or the Kappa Number (TAPPI method T-236), or the Roe Chlorine Number (TAPPI method 202), etc. Each of these tests is designed to determine the quantity of lignin present in the pulp fibers as a group and provides an indication of the total bleach requirement (the oxidizing agent demand of the pulp) in the bleaching step. The most commonly used of these tests is the Kappa number, which refers to the amount of material remaining in the pulp after cooking that can be oxidized by a standard solution of potassium permanganate. The material is often equated with the lignin content of the fibers.

The Kappa number test, as well as the other tests noted, is most commonly carried out by laboratory analysis of hourly samples of the digester output (samples are typically obtained at the last stage of the brownstock washer). This requires extracting a representative sample of the pulp, separating the pulp fibers from the cooking liquor, drying the pulp to oven-dry conditions, re-suspending the fibers, and treating this new mixture with one or more special agents, all under strict laboratory conditions. The laboratory analysis of the residual lignin takes approximately one hour and, therefore, is a poor method for providing process control feedback and cannot be used for feedforward control. A number of automatic sampling and testing devices have been tried but they have been mostly unsuccessful in providing accurate long-term results and do not reduce the one-hour delay between process and measurement of the residual lignin.

Still other devices are known which use the ultraviolet (UV) fluorescence properties of lignin to measure the lignin concentration. Such testing systems require very dilute lignin solutions to be prepared prior to measurement and, therefore, are not suitable for in-situ, or real-time, testing. Other ultraviolet absorption testing methods have attempted to measure the residual lignin in wood pulp by sampling the pulp every few minutes, preparing and diluting the sample, and circulating the sample into a loop where the UV light absorption is measured over a prescribed time period and the pulp concentration is measured independently. Even though this system provides for a faster method of testing than that of the laboratory method, it is still off-line.

One system known which provides for in-situ lignin testing is taught by U.S. Pat. No. 5,486,915, issued on Jan. 23, 1996, to Jeffers et al. This lignin analyzer uses a fluorescence technique to measure lignin concentration in undiluted samples of wood pulp. This method and apparatus require the use of fairly complex detection methods that use the radiation of the wood pulp with excitation light in a specific wavelength (in the range of 337 nm) in order for the residual lignin in the pulp to emit fluorescence. A spectral distribution of the fluorescence emissions is then determined and output signals produced to a signal processor that quantifies the residual lignin in the pulp by either a wavelength centroid or band ratio method.

Even though this system provides for in-situ, real-time analysis of the lignin concentrations, it is more effective during the early stages of the bleaching process where greater concentrations of lignin are present. In the later stages of the bleaching process the lignin content is reduced appreciably, thereby diminishing the fluorescence emissions of the pulp. This method also does not lend itself to measuring the later stages of the pulp process involving the brightness processing of the pulp, important in the formation of quality paper products requiring a high brightness level. A balance of bleaching agent to brightness must be determined in order not to degrade the strength of the pulp, not increase the cost of the bleaching operation, limit the exposure of personnel to toxic chemicals, and provide minimum impact on the environment.

SUMMARY OF THE INVENTION

Therefore, there is provided by the present invention a system for the continual, real-time, in-situ generation of a Kappa number used by a process control system to control the delignification of papermaking pulps. The system includes injecting broad-spectrum light energy from a light energy source into the pulp, or undiluted sample of the pulp, and collecting the resultant reflected light energy from a first light collector located near the point of injection and a second light collector located far from the point of injection. The reflected light energy collected by the first and second light collectors is analyzed by an associated near- and far-light analyzer. Each light analyzer generates analog output signals representing the intensity of the selected spectral wavelengths received.

A feedback arrangement conducts the light energy emitted by the light source to a location proximate the point of injection and then to an associated light analyzer. The light analyzer associated with the feedback arrangement generates analog output signals representing the intensity of the light energy emitted by the light source in the selected wavelengths.

The output signals from the near-, far- and feedback-light analyzers are transmitted to a measurement processing system that converts the analog signals to digital signals and passes the signals to a measurement computer. The measurement computer using a first preprogrammed algorithm normalizes the received data. Next, the measurements computer retrieves previously-stored coefficient values representing a model of the delignification process. The measurement computer, under control of a second preprogrammed algorithm, calculates a Kappa number representation using the calculated normalized values, the previously-stored coefficient values, and weighting data entered via a configuration computer. The Kappa number representation is then output to an input/output device that converts the Kappa number representation into a transmission form acceptable by the process control system and used to control the delignification process. Or, alternatively, the input/output output device can convert the Kappa number representation into an output signal compatible with visual display devices, recorders or printers.

Accordingly it is an object of the present invention to provide a system for providing in-situ, and on a continual and real-time basis, the Kappa number representation of a papermaking pulps process.

It is another object of the present invention to provide a system that can produce output signals representing a Kappa number used by a process control system to provide real-time, feed-forward control of the delignification of papermaking pulps.

BRIEF DESCRIPTION OF THE DRAWINGS

Other objects, features, and advantages of the present invention will be apparent from the following description of a preferred embodiment thereof, taken in conjunction with the accompanying drawings, in which:

FIG. 4 is a schematic block diagram of the measurement processing system in accordance to the present invention.

DETAILED DESCRIPTION OF THE INVENTION

Figure 1:
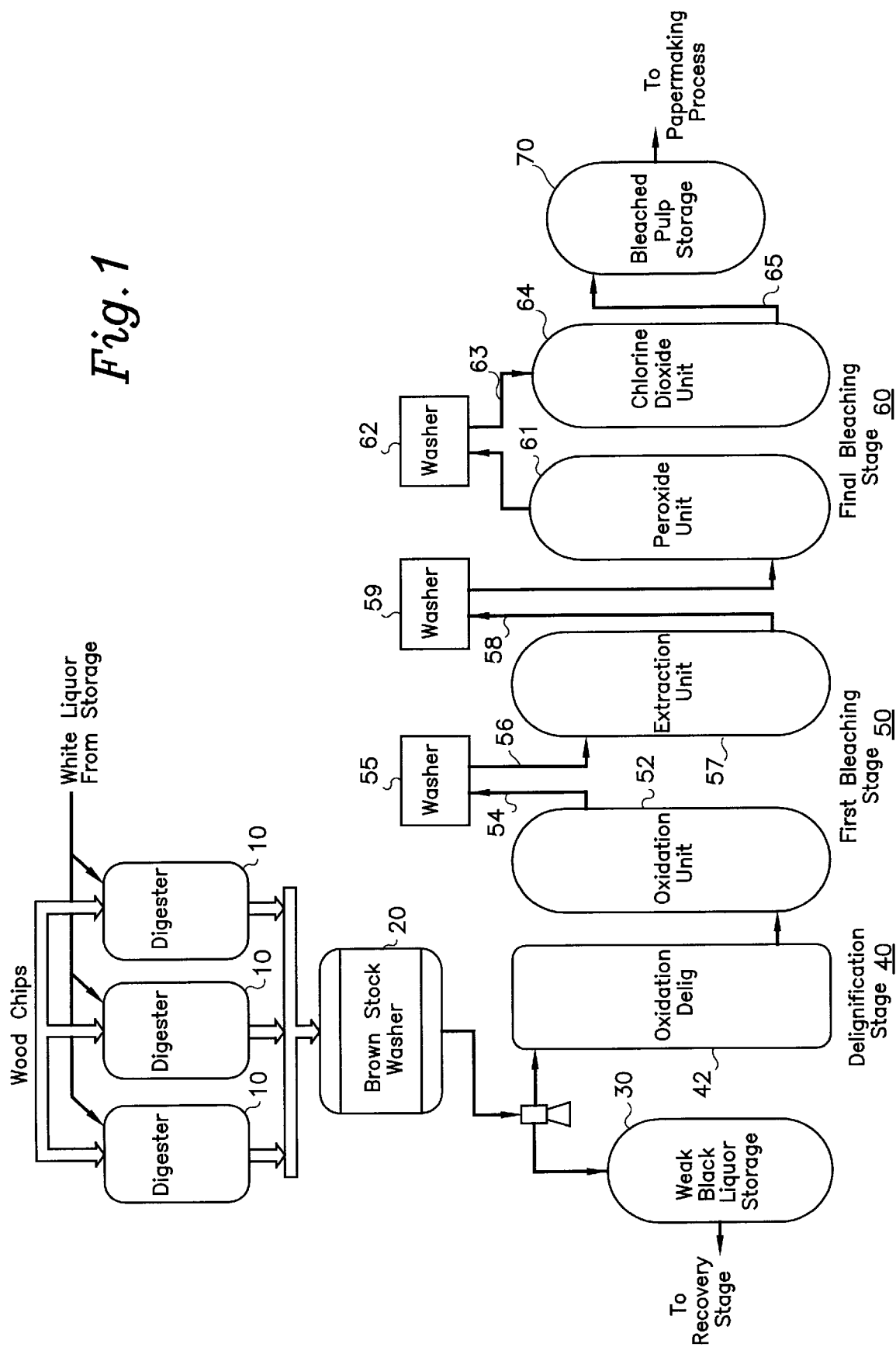
FIG. 1 shows a typical papermaking pulp process where the present invention is used to advantage.

Turning to FIG. 1, a typical process is shown for processing wood chips into papermaking pulp. Wood chips are fed into a plurality of digesters 10 along with a solution known as "white liquor". The white liquor in a kraft process is typically a mixture of sodium hydroxide (NaOH) and sodium sulfide ($Na_2S$). The wood chips and white liquor are cooked in the digesters 10 under controlled temperature and pressure to delignify or extract the binding agent, commonly known as lignin, from the cellulose fibers of the wood chips. Fluid drained from the digesters 10 during the delignification process is called "black liquor" and contains spent white liquor and lignin removed from the wood chips. This black liquor is removed by a one or more "brown stock" washers 20 prior to the pulp bleaching step. The black liquor at this stage is referred to as a "weak" black liquor and consists of sodium sulfate ($Na_2SO_4$), sodium carbonate ($Na_2CO_3$), sodium sulfide ($Na_2S$), and lignin organics. Weak black liquor is normally stored in containers 30 before being fed to a recovery operation.

A key element in the pulping manufacturing process is liquor recovery and power generation. Weak black liquor is fed to a system of multiple effects evaporators (not shown), where it is concentrated. This black liquor is then used as fuel in a furnace to manufacture steam for the papermaking pulp process and for power. A furnace recovery system (not shown) receives the smelt from the recovery furnace, which is dissolved into a "green liquor", clarified, and causticized with lime and sodium hydroxide (NaOH) to produce white liquor for the pulping process.

When the final product of the pulping process is to be a good-quality white paper, a bleaching process is introduced. The bleaching process varies according to the type of finished product the pulp is to become; therefore, the number of bleaching stages in the bleaching process and the type of bleaching agents used control the "whiteness" of the finished paper product. Typically, the bleaching process employs a delignification stage 40 and one or more bleaching stages, such as the first bleaching stage 50 and final bleaching stage 60. Each bleaching stage introduces oxygen, chlorine, chlorine dioxide, ozone or some other bleaching agent to the pulp. For this example, the bleaching process begins by feeding the pulp from the brown stock washer 20 to an oxygen ($O_2$) delignification unit 42. This provides further removal of any residual lignin remaining in the pulp after digestion and black liquor removal by the brown stock washer 20. The pulp is then pumped to a first bleaching stage 50, consisting of an oxidation unit 52, a washer 55, and an extraction unit 57. The pulp is pumped to the washer 55 from the oxidation unit 52 via conduit 54 and from the washer 55 to the extraction unit 57 via conduit 56. Oxygen, chlorine dioxide, or other bleaching agents are introduced into the pulp in this stage to further the brightening process. The brightening agents are removed by the extraction unit 57. The pulp is then pumped from the extraction unit 57, via conduit 58, to washer 59 and to peroxide unit 61 of the final bleaching stage 60. From the peroxide unit 61, the pulp is pumped to washer 62 and via conduit 63 to a chlorine dioxide unit 64. Finally, the brightened pulp is piped via conduit 65 to a bleached pulp storage unit 70. The bleached pulp is subsequently used as the raw material in the production of the finished paper product. It will be well understood by those skilled in the art that the bleaching process explained above can consist of more than the three bleaching stages shown in this example and that the present invention can be applied equally to a bleaching process having more than three stages of process.

The bleaching of the pulp dissolves any remaining lignin and renders white the remaining cellulose fibers. The intensity of whiteness and the term that the final paper product remains white are dependent on the remaining residual lignin in the cellulose fibers. It was, therefore, customary in prior art solutions to test either the residual lignin content of the cooking liquors or the pulp during the bleaching process as a determination of the measure of the effectiveness of the bleaching. The test of the residual lignin content can be used to determine the amount of bleaching agent that must be introduced into the various stages of the process to achieve the required brightness or whiteness of the pulp or, alternatively, the amount of time that the pulp must be kept in the bleaching process to achieve the desired brightness result.

The system of the present invention measures the reflectant qualities of the pulp during the delignification or bleaching process, also expressed as the reflectance of the pulp, as the means for determining the remaining lignin and, therefore, the effectiveness of the ongoing bleaching process. The present invention tests the pulp in-situ, continually, on a real-time basis and produces output signals in a form readily understood by those skilled in the art. For example, one of the widest used and most reliable measurement standard used in the industry today is the "Kappa number" documented in TAPPI procedure T236 cm-85, "Kappa Number of Pulp". This standard is defined as the number of milliliters of 0.1 normal potassium permanganate ($KMnO_4$) consumed by one gram of unbleached, moisture-free pulp during a specific reaction time under specific conditions. The Kappa number measures the remaining lignin content of the incoming pulp and, therefore, how much work must be done in bleaching.

The Kappa number output signal produced by the present invention can be visually displayed to a human operator via an output device such as an alphanumeric or chart display or printer. Additionally, the Kappa number can be expressed as data, or a process variable, to an automated process control system associated with the bleaching process. The process control system can subsequently control the introduction of bleaching agents to the various delignification and/or bleaching stages in accordance to the measured Kappa number. Additionally, since the measure is continuous, many small adjustments to the bleaching process can be made rather than fewer larger adjustments, leading to a finer, more robust control of the process. Therefore, the system of the present invention monitors the reflectance of the pulp and develops a measurement based on a Kappa number standard to represent the remaining lignin contained by the pulp. The Kappa number can then be used to determine the quantity of bleaching agents that need to be introduced during the bleaching stage of the pulpmaking process to achieve the desired result.

Figure 2:
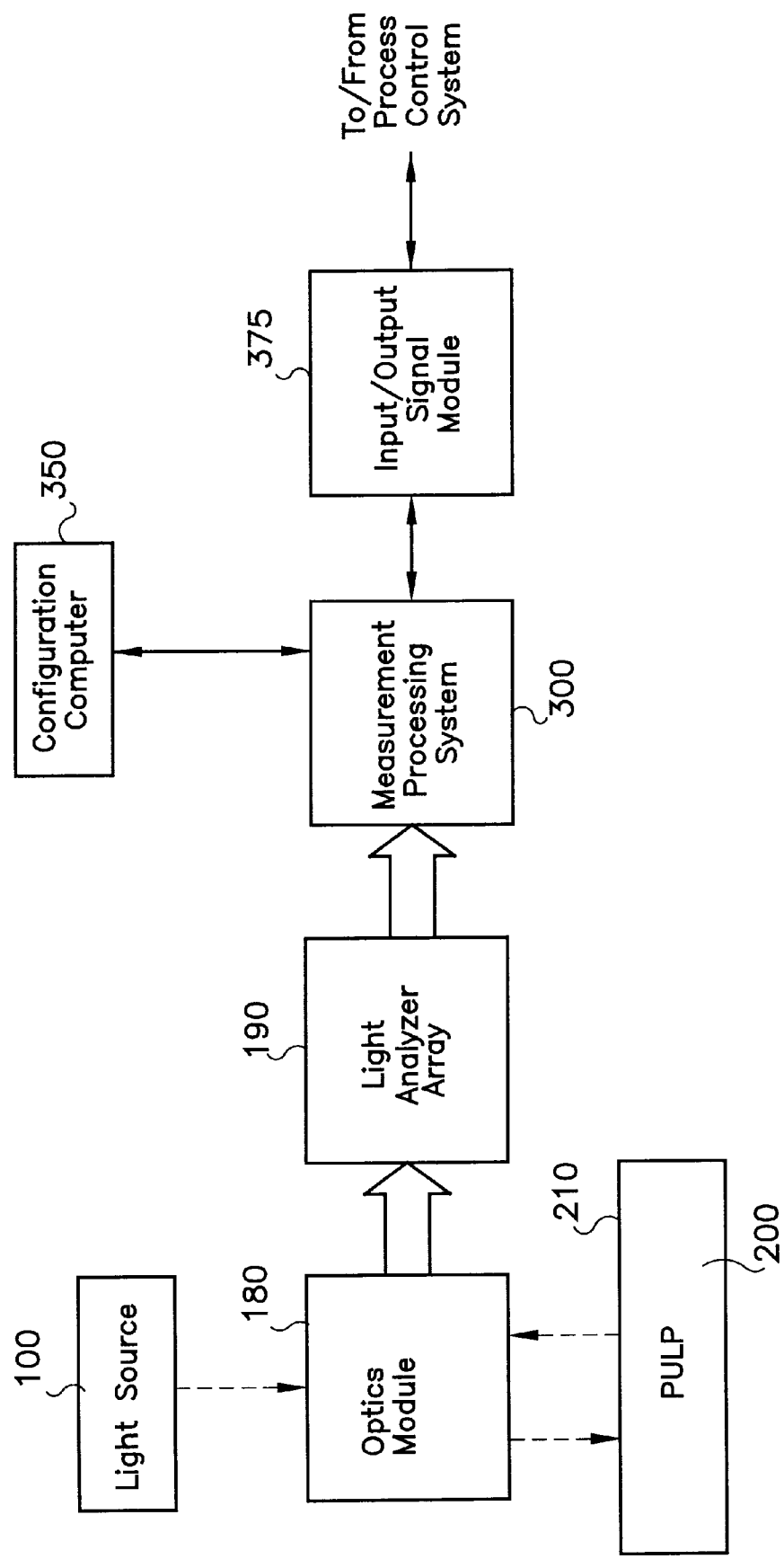
FIG. 2 is a schematic block diagram of the Kappa measurement system of the present invention.

Turning now to FIG. 2 of the included drawings, a schematic block diagram of the Kappa measurement system of the present invention is illustrated. The system of the present invention includes an optics module 180 that receives light energy from a light source 100. Light source 100 produces and emits light energy composed of a plurality of wavelengths. Optics module 180 injects the light energy into the pulp 200 which is conveyed within a conduit 210. The light energy reflected by the pulp 200 is collected by optics module 180 and transmitted to light analyzer 190. Light analyzer 190 analyzes the collected light energy and produces output signals representing the intensity of each wavelength collected. The wavelength intensities are next transmitted to a measurement processing system 300 where the reflectance data is processed using a stored model representing the delignification process and offsets, gains, or other tuning data entered via configuration computer 350. The measurement processing system 300 uses a preprogrammed algorithmic formula to translate the collected wavelength intensities and user-input data into a Kappa number representation. The resultant Kappa number representation is output to an input/output signal module 375. The signal module 375 converts the Kappa number from the measurement processing system into an output signal that can be read by a process control system. For example, module 375 can convert the Kappa number representation into a 4 mA-to-20 mA current loop output that is commonly used in the process control industry to pass control variable information from field devices to a controller. Alternatively, the data can be output as serial or parallel digital data to a data network for transmission to the process control system. It will be well understood to those skilled in the art that the Kappa number representation output by module 375 can be converted into any one of a number of presently-known communication methods employed between field devices and processing systems and used for exchanging information and data.

Figure 3:
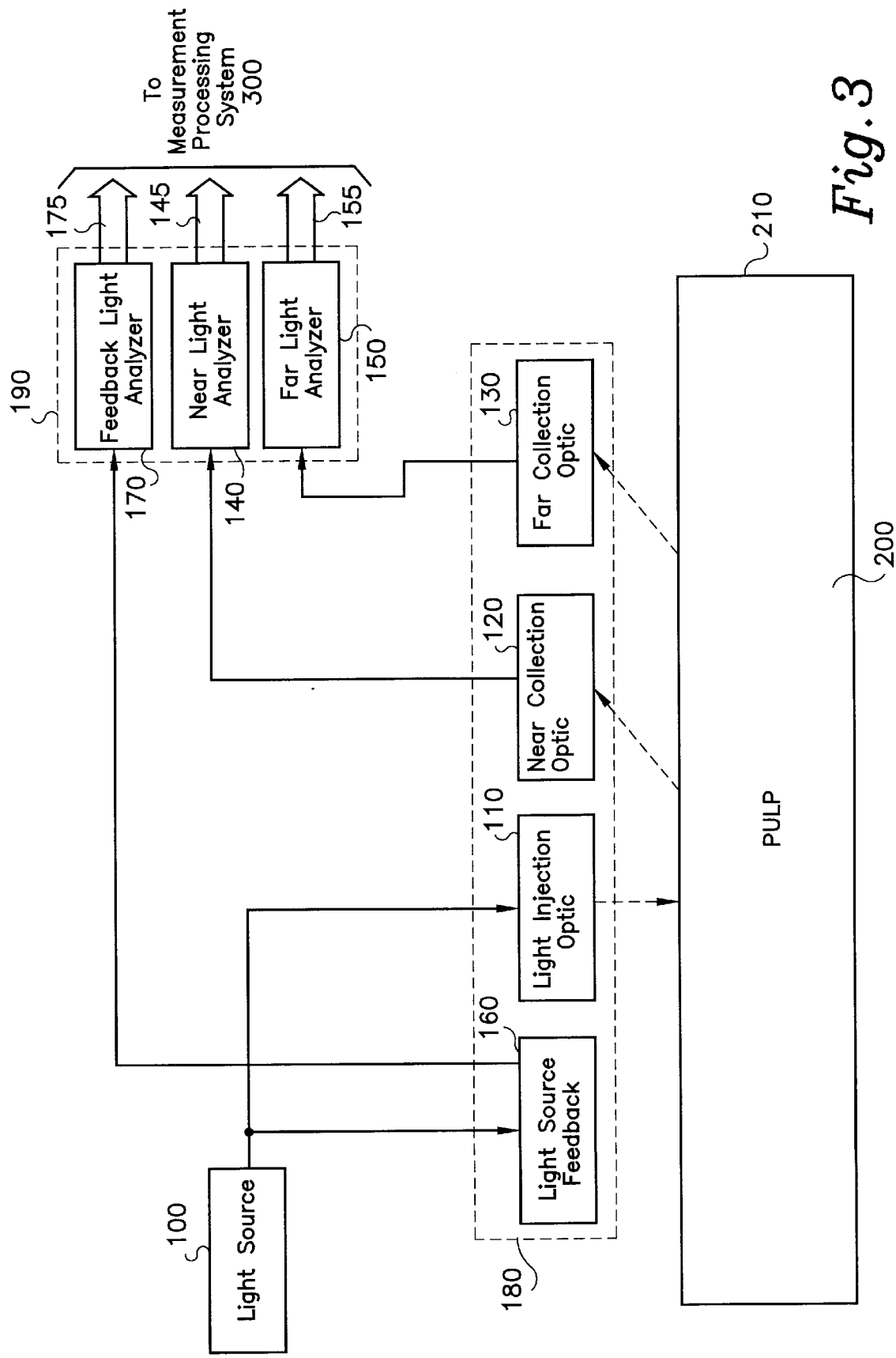
FIG. 3 is a schematic block diagram illustrating the major components of the optics module and light analyzer array in accordance to the present invention.

Turning now to FIG. 3, a more detailed explanation of the functionality of the optics module 180 and light analyzer 190 of the present invention will be made. Light energy having at least the blue, green, amber and infrared wavelengths is produced and emitted by a light source 100 and is delivered to the pulp 200, or an undiluted sample of pulp, by light injection optics 110. The light source 100 can be a quartz halogen bulb, or any one of the many devices known by those skilled in the art, that can produce and emit light energy in at least the above-mentioned spectra of wavelengths. The pulp 200 is typically conveyed through a pipe or conduit 210 that forms a part of the overall plant bleaching process. For example, with renewed reference to FIG. 1, the present invention can be used to sample the pulp flowing in conduit 44 after the $O_2$ delignification unit 42, or in conduit 54 after oxidation unit 52. Alternatively, conduit 210 can comprise a bypass line from any of the aforementioned bleaching process conduits that convey a portion of the total pulp taken from the conduits.

Some of the injected light energy is absorbed by the pulp and some reflected (thus it is re-radiated) correlating to the pulp properties. The light energy reflected by pulp 200 is collected by near-collection optic 120 and far-collection optic 130 and is delivered to near-light analyzer 140 and far-light analyzer 150, respectively. Near-collection optic 120 is located adjacent to injection optic 110. Near-collection optic 120 is arranged to collect the light energy reflected near the injection optic 110 that is scatter reflected by the pulp. A portion of the light energy injected into the pulp 200 penetrates farther into the pulp and is reflected farther from the point of injection. This light energy is collected by far-collection optic 130.

The near-light analyzer 140 and far-light analyzer 150 detect and measure the intensity of each of the wavelengths of light energy reflected by pulp 200 and collected by their respective collection optics 120 and 130. Near-light analyzer 140 and far-light analyzer 150 produce outputs 145 and 155 respectively, representing the intensity of the light energy received in each of the blue, green, amber and infrared wavelength by each light analyzer 140,150. For example, output 145 includes four distinct analog voltage output signals representing the intensity of a respective blue, green, amber and infrared wavelength collected. Therefore, four separate and distinct analog voltage output signals representing the wavelength intensities collected are produced by each of the near and far-collection optics 140 and 150.

In order to provide a baseline of the intensity of each wavelength produced by the light source 100, the present invention includes a light source feedback arrangement. The light energy produced by light source 100 is further delivered to a light source feedback arrangement 160, which is located proximate the pulp 200. The light energy is then conveyed from the feedback arrangement 160 to a feedback-light analyzer 170. The feedback-light analyzer 170 detects and measures the intensity of each of the blue, green, amber and infrared wavelengths of light energy produced by the light source 100 and produces four analog voltage output signals, shown generally as 175, representing the intensity of each of the aforementioned wavelengths produced by light source 100. The feedback arrangement can also be used to ascertain a drop-off of the light energy intensity produced by light source 100, due to its failure or imminent failure.

A better understanding of the optics module 180 and light analyzer 190 as well as the means used in converting the collected and feedback light into output signal representations may be had by reference to applicants' co-pending application, Ser. No. 08/988,972, titled, "An Apparatus Used In Determining the Degree of Completion of a Processed Medium", and which application is incorporated herein by reference.

Turning now to FIG. 4 of the included drawings, the major components of the measurement processing system 300 is shown. Analog voltage signals 145, 155 and 175 from light analyzer 190 are connected to signal amplifier 301 where they are amplified. The signals are then output to an analog-to-digital converter 302, where they are digitized into a matrix of sensed component values. The digitized component values representing output signals 175, 145 and 155 are next applied to measurement computer 303 where they are processed. Stored within measurement computer 303 is an operating system and conversion algorithms that act on the component values received from analog-to-digital converter 302. During operation of the system the measurement computer first establishes a normalized relationship between the wavelength intensities received by the near- and far-collection optics and the wavelength intensities produced by the light source. This is carried out by dividing each of the reflected wavelength intensities collected from each collection optic by the wavelength intensities produced by the light source.

The mathematical relationship for the normalization is:

Nx/Fx=Vnx (for the wavelengths and intensities collected by near-collection optic 120)

FRx/Fx=Vfrx (for the wavelengths and intensities collected by far-collection optic 130)

where:

x=one of the blue, green, amber and infrared wavelengths;

Nx=the intensity of the x wavelength collected by the near-optic collector;

Fx=the intensity of the x wavelength feedback signal;

Vnx=the resultant normalized value for the specific near-x wavelength;

FRx=the intensity of the x wavelength collected by the far-optic collector; and

Vfrx=the resultant normalized value for the specific far-x wavelength.

A normalized reflectance value is calculated for each near wavelength and each far wavelength and the values stored in a normalized reflectance data storage device 304 along with a time stamp of the time when the wavelengths where collected from a source of time signals 326. The source of time signals 326 can be any device or scheme that will output an accurate signal representing chronological time.

A set of coefficient values is stored in a coefficient value storage device 305. The coefficient values are also time stamped. This set of coefficient values includes a value for each near and far wavelength that the system of the present invention processes. The coefficient values are derived from detailed laboratory analysis of the particular pulping or bleaching process and a process prior history. In other words, the coefficient values stored in the coefficient value storage device comprise a set of constant values that represent a model of the "ideal" values for each reflected wavelength received at a particular interval of time. The coefficient values are used with the normalized reflectance values to calculate the Kappa number representation.

Overall system gain (G) and offset value or bias (O), or other tuning data, are entered into measurement computer 303 by configuration computer 350. Configuration computer 350 can be connected directly to the measurement computer 303 by a serial or parallel data line 351 or, alternatively, located remote from the measurement computer 303. For a remotely-located configuration computer, line 351 may be replaced by any of the known methods for establishing a remote communications link between two or more computing devices. This configuration data is transmitted from the configuration computer 350 to the measurement computer 303 and allows the fine tuning of the resultant Kappa number generation based on the particularity of the bleaching process. Similarly, the configuration computer 303 downloads either directly, or remotely the coefficient values to the coefficient values storage device 305.

The Kappa number representation is derived using the normalized reflectance values stored in data storage device 304, the coefficient values stored in the coefficient values storage device 305, for a specific point in time and the configuration data downloaded to the measurement computer 303. That is, the normalized reflectance values stored in device 304 at a particular point in time are processed with only the coefficient values from device 305 that have a like time stamp. For example the normalized reflectance values stored at 10:00 a.m. are calculated with coefficient values stored in device 305 that are time stamped to be used with normalized reflectance values collected at 10:00 a.m.. For any particular point in time, the system uses the following algorithm routine to calculate the Kappa number:

(KnbVnb+KngVng+KnaVna+KnirVnir+KfrbVfb+ KfrgVfrg+KfraVfra+KfrirVfrir) * G+O where:

Knb=the near coefficient value for the blue wavelength;

Vnb=the normalized near blue wavelength received;

Kfrb=the far coefficient value for the blue wavelength;

Vfrb=the normalized far blue wavelength received;

and where;

b=blue wavelength;

g=green wavelength;

a=amber wavelength; and ir=infrared wavelength.

The result of the above-identified algorithm is a Kappa number representation of the bleachability of the pulp. The Kappa number value calculated by the measurement computer is output to input/output module 375 and converted into one of the above-mentioned output signal types for output to a display, a chart recorder, printer, or process control system. The Kappa number can be used by the process control system to control the delignification or the amount of bleaching agents introduced in the pulping process in order to achieve the desired finished paper product.

It will be appreciated by those skilled in the art that the process control system can also be used to enter the gain or offset values via the input/output signal module. Additionally, the measurement computer can include a datalogging capability tasked in recording and storing the raw wavelength data or processed Kappa number over a period of time. This data can then be downloaded to the process control system via the input/output signal module for modeling, process history analysis or comparison with laboratory samples.

The present invention has been described with particular reference to the preferred embodiments thereof. It will be obvious that various changes and modifications can be made therein without departing from the spirit and scope of the invention as defined in the appended claims that characterize a system for the continual, real-time, in-situ generation of a Kappa number used by a process control system to control the delignification of papermaking pulps that includes injecting broad-spectrum light energy from a light energy source into the pulp and collecting the resultant reflected light energy from a near-and far-light collector. The reflected light energy collected by the light collectors is analyzed by an associated light analyzer, that generates analog output signals representing the intensity of selected wavelengths of light energy received by the light collectors. An included feedback arrangement conducts the light energy emitted by the light source to a location proximate the point of injection and then to an associated light analyzer that generates analog output signals representing the intensity of the light energy emitted by the light source in selected wavelengths. The output signals from the light analyzers are transmitted to a measurement processing system that converts the analog signals to digital signals and passes the signals to a measurement computer. The measurement computer, using preprogrammed algorithms, processes the received reflectance output signals along with previously-stored coefficient values that represent a model of the delignification or bleaching process, and, along with configuration data, generates an output signal representing a Kappa number representation. The output signal from the measurement computer is converted by an input device into a signal form acceptable by the process control system, where it is used to control the delignification process in accordance to the Kappa number representation.

What is claimed is:

1. A system for the continual, real-time, in-situ generation of a Kappa number used by a process control system to control the delignification of papermaking pulps, said system comprising:

a light source for generating light energy in a plurality of wavelengths;

an optics module connected to said light source for injecting said light energy into said pulp and subsequently collecting said light energy reflected by said pulp from a plurality of collector locations;

a feedback device connected to said light source and associated with said optics module, arranged to return light energy from a location proximate said optics module;

a light analyzer array connected to said optics module and said feedback device arranged to receive said reflected light energy collected from said plurality of collector locations and said light energy returned by said feedback device and to determine the intensity of each wavelength of light energy received from each respective collector location and from said feedback device and to generate a respective plurality of output signals indicative thereof;

a measurement processing system connected to said light analyzer array, to a source of coefficient values and to a configuration device, said measurement processing system arranged to receive each respective plurality of output signals from said light analyzer, coefficient values from said source of coefficient values and configuration data from said configuration device and, in accordance to preprogrammed algorithmic routines stored in said measurements processing system, to develop an output signal representing a Kappa number; and an output signal module connected to said measurement processing system and to said process control system, said output module receiving said output signal from said measurement processing system and converting said output signal into a transmission form acceptable by said process control system whereby said process control system controls the delignification of said papermaking pulp in accordance to the Kappa number representation.

2. The system as claimed in claim 1, wherein said optics module includes an injection optic whereby said injection optic injects said light energy into said pulp.

3. The system as claimed in claim 2, wherein said optics module further includes a near-collection optic located proximate said injection optic, and a far-collection optic located farther from said injection optic whereby light energy reflected by said pulp near said injection optic is received by said near-collection optic and said light energy reflected by said pulp farther from said injection optic is received by said far-collection optic.

4. The system as claimed in claim 2, wherein said feedback device collects said light energy from said injection optic immediately prior to said light energy being injected into said pulp.

5. The system as claimed in claim 1, wherein said light source is a halogen lamp that generates and emits light that includes at least the blue, green, amber and infrared wavelengths.

6. The system as claimed in claim 5, wherein said light analyzer array includes a near-light analyzer connected to said near collection optic, a far-light analyzer connected to said far-collection optic and a feedback-light analyzer connected to said feedback device, whereby said near-light analyzer receives said light energy reflected by said pulp and collected by said near-light collector, said near-light analyzer arranged to produce a first set of analog output signals representing the respective intensity of each of the blue, green, amber and infrared wavelengths received.

7. The system as claimed in claim 6, wherein said far-light analyzer receives said light energy reflected by said pulp and collected by said far-light collector, said far-light analyzer arranged to produce a second set of analog output signals representing the respective intensity of each of the blue, green, amber and infrared wavelengths received.

8. The system as claimed in claim 6, wherein said feedback-light analyzer receives said light energy returned from said injection optic, said feedback-light analyzer arranged to produce a third set of analog output signals representing the respective intensity of each of the blue, green, amber and infrared wavelengths generated by said light energy source and returned from said injection optic immediately prior to said light energy being injected into said pulp.

9. The system as claimed in claim 8, wherein said measurement processing system includes:
- a signal amplifier arranged to receive and amplify said first set, said second set and said third set of analog output signals;
- a analog-to-digital converter connected to said signal amplifier arranged to receive said first set, said second set and said third set of amplified analog output signals, thereby converting said first set, said second set and said third set of amplified analog output signals to a first set, a second set and a third set of digital signals;
- a measurements computer connected to said analog-to-digital converter, said measurements computer receiving said first set, said second set and said third set of digital signals;
- a data storage device connected to said measurements computer; and
- said measurements computer, under control of a preprogrammed normalizing algorithm routine, processes said first, said second and said third set of digital signals and develops a first set and a second set of normalized values whereby said first set and said second set of normalized values are stored in said data storage device.

10. The system as claimed in claim 9, wherein said measurements computer further includes a coefficient value storage device having first and second coefficient values stored therein, and under control of a preprogrammed Kappa number-generating algorithm retrieves said first set and said second set of normalized values from said data storage device and said first and second set of coefficient values from said coefficient value storage device, and including said configuration data from said configuration device, calculates and develops said output signal representing said Kappa number.

11. The system as claimed in claim 10, wherein said measurements computer further includes a source of time signals and said first set and said second set of normalized values are stored including a time marker from said source of time signals and said first set and said second set of coefficient values include coefficient values relating to a specific point in time whereby, said preprogrammed Kappa number-generating algorithm retrieves said first and said second set of coefficient values corresponding to a specific point in time in accordance to said time marker, and including said configuration data from said configuration device, calculates and develops said output signal representing said Kappa number.

12. The system as claimed in claim 11, wherein said configuration device is a computer connected locally or remotely to said measurements computer and said user-entered configuration data comprises system gain (G) and offset bias (O).

13. The system as claimed in claim 12, wherein said preprogrammed Kappa number-generating algorithm comprises:

$$(K_{nb}V_{nb} + K_{ng}V_{ng} + K_{na}V_{na} + K_{nir}V_{nir} + K_{frb}V_{fb} + K_{frg}V_{frg} + K_{fra}V_{fra} + K_{frir}V_{frir}) * G + O$$

where:
- $K_{nb}$ = the near coefficient value for the blue wavelength;
- $V_{nb}$ = the normalized near blue wavelength received;
- $K_{frb}$ = the far coefficient value for the blue wavelength;
- $V_{frb}$ = the normalized far blue wavelength received;

and where;
- b = blue wavelength;
- g = green wavelength;
- a = amber wavelength; and
- ir = infrared wavelength.

14. The system as claimed in claim 13, wherein said output module converts said output signal representing a Kappa number into a 4 mA-to-20 mA current loop.

15. The system as claimed in claim 13, wherein said output module converts said output signal representing a Kappa number into serial or parallel formatted digital data.

16. The system as claimed in claim 13, wherein said output module converts said output signal representing a Kappa number into a output signal compatible with display, charting or printing devices.

17. A system for the continual, real-time, in-situ generation of a Kappa number used by a process control system to control the delignification of papermaking pulps, said system comprising:
- means for generating light energy having a broad spectral distribution;
- means for injecting said light energy into said pulp and subsequently collecting said light energy reflected by said pulp from a plurality of collector locations;
- means for feeding back said light energy from a location proximate said means for injecting prior to said light energy being injected into said pulp;
- means for analyzing said reflected light energy collected from said plurality of collector locations and said means for feeding back arranged to determine the intensity of individual spectra of light energy collected from each respective collector location and from said means for feeding back and to generate a respective plurality of output signals indicative thereof;
- means for entering coefficient values and configuration data;
- means for processing each respective plurality of output signals together with said coefficient values and configuration data in accordance to preprogrammed algorithmic routines stored in said means for processing for generating an output signal representing said Kappa number; and
- means for converting said output signal into a transmittable form acceptable by said process control system whereby said process control system controls the delignification of said papermaking pulp in accordance to said Kappa number representation.

18. The system as claimed in claim 17, wherein said plurality of spectral bands are comprised of at least the blue, green, amber and infrared wavelengths.

* * * * *